United States Patent [19]

Wyatt

[11] Patent Number: 4,490,042
[45] Date of Patent: Dec. 25, 1984

[54] METHOD FOR DETERMINING THE PROPERTIES OF WINE

[76] Inventor: Philip J. Wyatt, 1939 Laguna St., Santa Barbara, Calif. 93101

[21] Appl. No.: 270,545

[22] Filed: Jun. 4, 1981

[51] Int. Cl.³ .......................................... G01N 21/00
[52] U.S. Cl. ................................... 356/340; 356/343
[58] Field of Search ........................ 356/338, 340. 343

[56] References Cited

U.S. PATENT DOCUMENTS

| | | | |
|---|---|---|---|
| 3,202,826 | 8/1965 | Greathouse | 356/341 |
| 3,624,835 | 11/1971 | Wyatt | 356/343 |
| 3,730,842 | 5/1973 | Wyatt | 356/340 X |
| 3,754,830 | 8/1973 | Phillips | 356/340 |
| 3,770,351 | 11/1973 | Wyatt | 356/343 X |
| 3,928,140 | 12/1975 | Wyatt et al. | 356/341 |
| 4,173,415 | 11/1979 | Wyatt | 356/343 X |
| 4,263,511 | 4/1981 | Hirschberg | 356/340 |

FOREIGN PATENT DOCUMENTS 0564599 11/1977 U.S.S.R. .......................... 356/338

OTHER PUBLICATIONS

Bickel, W. S., "Optical system for light scattering experiments", Applied Optics, vol. 18, No. 11, pp. 1707–1709, Jun. 1, 1979.

*Primary Examiner*—Bruce Y. Arnold

[57] ABSTRACT

A method for deriving a quantitative measure of a beverage which will correlate to the subjective sensory stimuli response of beverage consumers. The method comprises illuminating an aliquot or a dilution thereof with a beam of monochromatic light, measuring the light scattering pattern produced, comparing this pattern to that of a reference pattern, and using the difference between the two patterns as the quantitative measure. A variation of the method is disclosed wherein a number of measurements at a selected set of angles over a period of time are measured and, at each selected angle, the intensity is measured several times. In this method, the average of the intensities so detected at each selected angle is determined, and the numerical set of the fluctuation of each detected value from the average is used to characterize the beverage.

18 Claims, 3 Drawing Figures

METHOD FOR DETERMINING THE PROPERTIES OF WINE

BACKGROUND

The proliferation rate of small, independent wineries throughout the world is exceeded only by activity in the publication of books and periodical articles on wine tasting and appreciation. A mystique has thereby evolved which renders the average consumer frustrated in the selection and judgement of wines that he might purchase. M. A. Amerine and C. S. Ough, for example, noted authorities in enology, point out in their book *Wine and Must analysis* (John Wiley & Sons, New York 1974) that literally ". . . thousands of methods have been developed for analysing wines . . . " during their manufacture. These are primarily chemical/analytical methods to which must be added a variety of sensory testing methods and techniques. Many of these sensory tests are discussed in the book by Amerine with R. M. Pangborn and E. B. Roessler *Principles of Sensory Evaluation of Foods*, (Academic Press, New York and London 1965). For the consumer, however, many of these methods seem more hyperbole than fact and he needs some more rapid and simple means by which the quality of a wine may be established. On careful reflection, all qualities of a wine (such as taste, aroma, color, calirty, etc.) must exist by virtue of the particle types present, be they molecules, bacteria, or even pieces of grape residues. It has been discovered that an examination of the light scattering properties of wine can yield important parameters correlatable with an average consumer's opinions or preferences. Although turbidity and nephelometric measurements are made during the production of wines, such methods only represent means by which a crude estimate of the amount of suspended solids may be made. To this time, the relationship of the light scattering properties of a wine to a typical consumer's opinion of the wine has not been explored.

SUMMARY OF THE INVENTION

The present invention provides for a method of evaluating the quality of a wine as perceived by an average consumer from a measurement of the wine's differential light scattering (DLS) pattern. Although the present invention emphasizes the properties of wine, it may be equally well applied to beer, spirits, and other reasonably clear beverages. In the preferred embodiment of the invention, an aliquot of wine is carefully decanted from its bottle, diluted with filtered deionized water, placed in a cuvette of the type described by Berkman and Schoefer in U.S. Pat. No. 3,701,620, and illuminated diametrically by means of a vertically polarized fine laser beam, such as is produced by a He-Ne laser ($\lambda=632.8$ nm) or an Argon-ion laser ($\lambda=514.5$ nm, and others). An array of detectors, or a rotating single detector, measures the scattered light intensity as a function of scattering angle, generally in a plane perpendicular to the plane of polarization of the laser. This scattering variation is then recorded digitally, or by a strip chart recorder or similar means, and compared with a stored library of such scattering patterns; or the pattern itself and its fluctuations are used to derive a quantitative measure of the diluted wine sample.

DETAILED DESCRIPTION OF THE INVENTION

The present invention consists of a method and apparatus by which means the properties of a wine (or other beverage) of importance to a typical consumer may be objectively represented in graphical or numerical form and, thereby, be capable of comparison with a library or catalog of his personal standards, or be rated in a straightforward manner without recourse to the subjective pronouncement of wine judging authorities. Naturally the invention will have application in the fabrication of wine and other beverages, as well, as those properties most important for the consumer must be considered also by the manufacturer.

Figure 1:
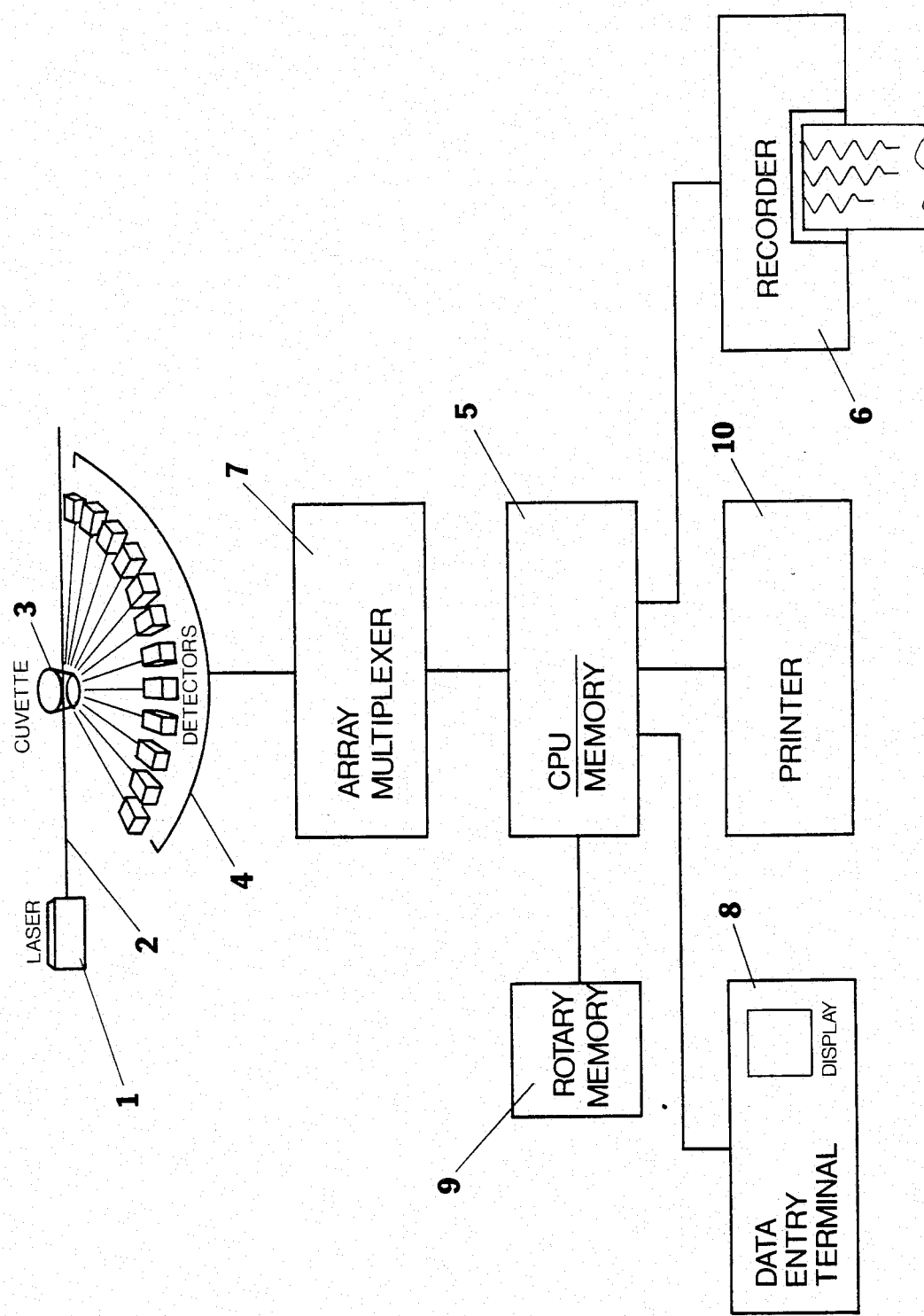
FIG. 1 presents a diagram of the preferred embodiment of the apparatus. It includes a laser, a sample holder, a detector array, an electronic processing unit, a recorder, a rotating memory, and an input device.

FIG. 1 represents a preferred embodiment of the invention whereby a laser 1 produces a vertically polarized monochromatic beam 2 which transverses diametrically a cuvette 3 containing a diluted aliquot of the wine being tested. A detector array 4 is placed about the cuvette subtending a range of scattering angles, $\theta$, between say 20° and 140° or any other reasonably broad range. The detected signals are amplified and stored digitally or plotted graphically by means of the digital processor 5 or analog recorder 6 shown. The digital processor with memory 5 includes an A/D multiplexer 7 of the type manufactured by Burr Brown, a central processor input terminal 8 with display by which means the instrument may be provided with sampling and other instructions by the user, and a storage device 9 such as a rotary memory or bubble memory. The measured and stored information may be immediately analysed and the results presented on the display or by means of a printer 10 or recorder 6.

Although the preferred embodiment of the invention incorporates a monochromatic vertically polarized light source such as a laser, the measurement could also be performed with an incoherant light source and even white light source or a source operating at several wavelengths simultaneously. The light sources, in addition, need not be polarized. These alternate light sources would not generally provide the resolution of the preferred embodiment, but nevertheless would prove sufficient for many measurements.

Figure 2:
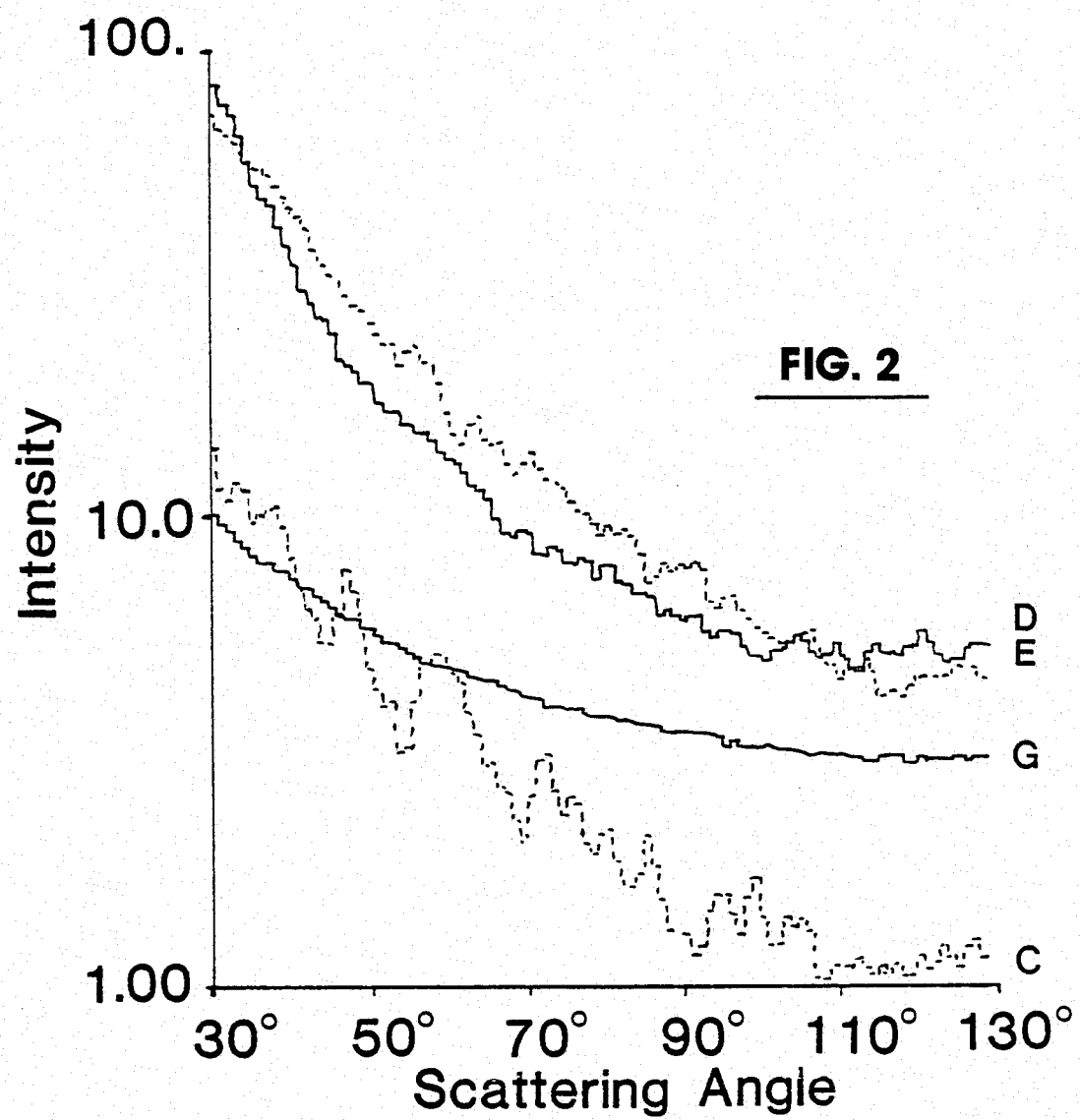
FIGS. 2 and 3 present the differential light scattering patterns obtained from 7 varietal Pinot Noir wines diluted with deionized water at a ratio of 1 part wine to 9 parts water.
Figure 3:
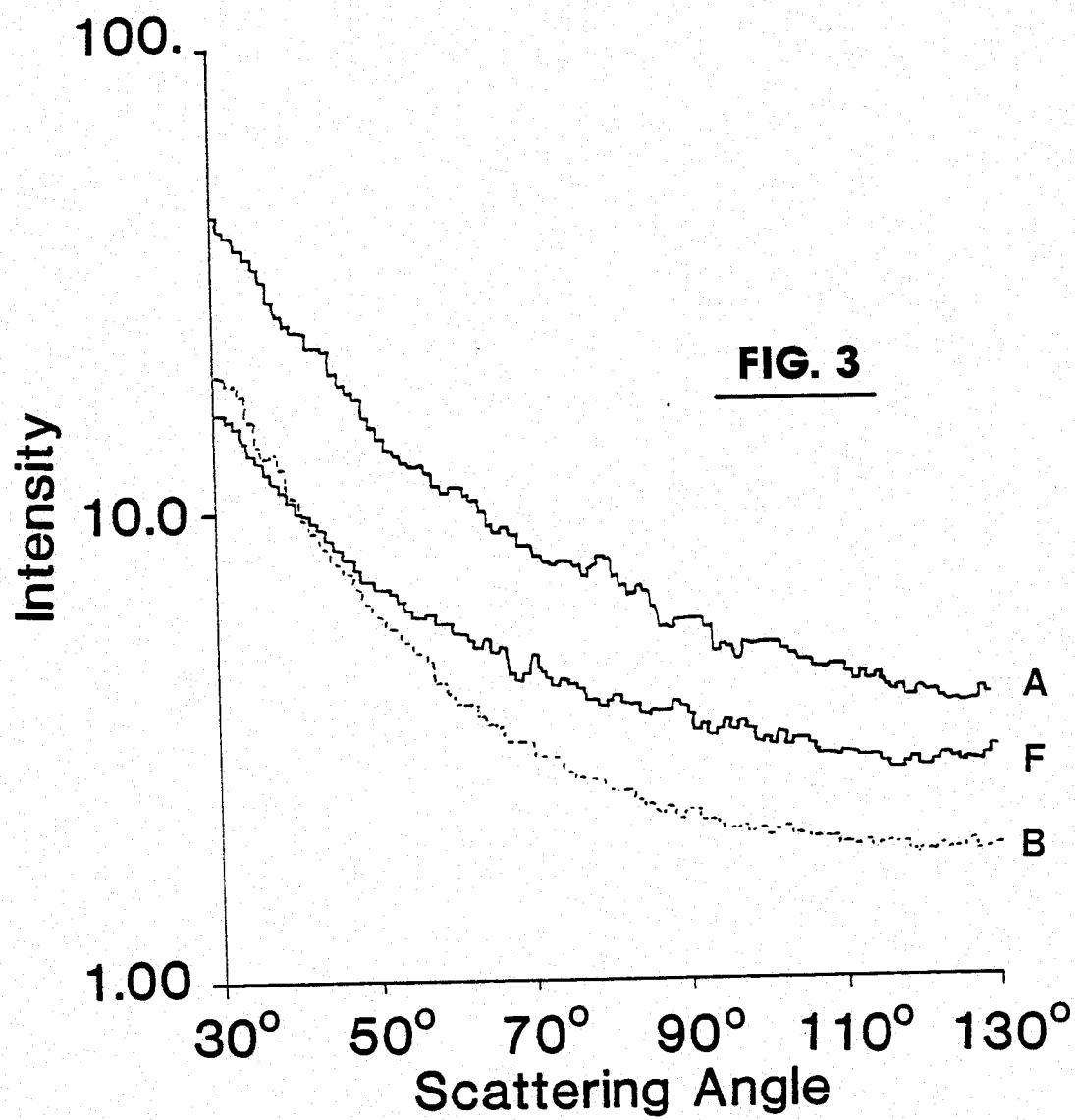

The apparatus of FIG. 1 will result in the acquisition and storage of one or more differential light scattering (DLS) patterns of the diluted sample. The DLS pattern represents the variation of scattered intensity as a function of detector angle. The pattern is preferably stored as the logarithm of the scattered intensity as a function of angle. In the preferred embodiment of this invention, the set of discrete detectors may number 10 to 15 and lie in a plane. If required, the values of the scattered intensitites between the detector locations may be readily deduced by interpolation. FIGS. 2 and 3 present sets of DLS patterns labeled A through G as measured from diluted aliquots of seven different brands of the varietal wine Pinot Noir. For these patterns, an apparatus having a scanning photomultiplier was employed and the logarithm of the scattered intensity values were stored at one degree intervals.

In the preferred embodiment of the invention, the DLS patterns are recorded in a plane perpendicular to the laser plane of polarization. Other detector configurations outside of this plane are also possible and represent variations of the basic structure of the preferred apparatus.

The recorded DLS patterns represent the superposition of the scattering of all the illuminated particles seen by the detector system. Very small particles, such as molecules will scatter vertically polarized light isotropically and proportional to the square of the molecular volume. Slightly larger particles (say, in the range of 10 to 200 nm in diameter) will scatter light somewhat peaked in the forward direction as shown, for example, in the *Atlas of Light Scattering Curves*, (Science Spectrum, Inc., Santa Barbara 1975). Once the particle size is comparable to the wavelength of the incident radiation, the DLS patterns become quite complex and depend intimately upon particle shape, dielectric composition, structure, and dimension, as well as distributions of these parameters. In this so-called resonace region, the DLS pattern is no longer a monotonically decreasing function of angle, but rather displays pronounced variations very much like a diffraction pattern. Particles that are very large compared to the wavelength of the incident light scatter primarily by means governed by geometrical optics plus diffraction. Irregular particles thus often produce specular effects, i.e. highly directional scattering, as well.

In addition to scattering incident light, many types of particles absorb light. These absorption effects are often very important for assaying the presence of certain types of particles. Many wines and beverages such as beer are pigmented because they strongly absorb certain wavelengths of incident white light and reflect or scatter others. In order that the light scattering properties of wine be more readily apparent by the present invention, it is important that the samples exhibiting even modest pigmentation be diluted, preferably by a factor of about 10:1.

As I have mentioned earlier, the properties of a wine (or other beverage) of importance to a consumer such as taste, aroma, and clarity arise by virtue of the particles present. Since the light scattering properties also are due to the particles present, I have examined the correlation between the physical parameters expressed in a DLS pattern with the sensory responses of a typical set of consumers. Table I presents the details of wine quality as perceived by a random panel of 8 consumers, none of whom was a professional wine taster.

TABLE I

| | Wine Qualities (Pinot Noir) | | |
|---|---|---|---|
| ID | Cost* | Panel+ Rank | Comments# |
| A | $3.75 | 4 | NR |
| B | 3.75 | 5 | NR |
| C | 5.00 | 3 | Y, T |
| D | 3.15 | 7 | SP, T, H |
| E | 6.50 | 6 | T, V, H |
| F | 7.00 | 2 | P, N |
| G | 12.00 | 1 | G, N, Y |

*Cost vary from store-to-store. These were prices at one store on date of purchase.
+Physicist, mathematician, electrical engineer, office manager, X-ray technician, coin dealer, electromechanical assembler, and attorney.
G: good; SP: soda pop after taste; T: thin; P: pleasant; N: nice flavor; NR: no resemblence to a Pinot; V: vegetable taste; H: horrible; Y: young.

The seven wines listed produced the DLS patterns shown in FIGS. 2 and 3 following a 10:1 dilution with deionized water. Because the natural pigmentation of these wines is red, the use of a He-Ne laser operating at 632.8 nm insures that very little light is absorbed and that the recorded DLS patterns characterize the scattering properties of the ensemble of molecules and particles present.

As may be seen from FIGS. 2 and 3, the degree of unpleasant taste as determined by the panel of consumers (Table I) correlates well with the degree of noise and relative amplitude in the recorded signals. The smoother and flatter curves correspond to better tasting wines; a predominance of large particles tending to affect simultaneously both taste and light scattering properties.

The total material present within each sample is manifest from the vertical position of the DLS pattern. Thus if two samples contained identical types and distributions of molecules and other particulates, the sample containing the greatest concentration would yield the pattern of greatest intensity. The relative height of the pattern, however, is not necessarily proportional to the number of particles present. Indeed, in the molecular regime [cf. M. Kerker's article in *Industrial and Engineering Chemistry* vol. 60, page 30 (1968), the scattered intensity from a particle is proportional to the square of its volume (Rayleigh region). Thus a particle 10 nanometers in diameter will generally scatter four times as much light as one with half that diameter. The slope of the DLS pattern near forward scattering (small scattering angles) becomes steeper as the average particle size increases.

Wines F and G have the shallowest slopes and essentially the smoothest DLS patterns. At large scattering angles the patterns are nearly horizontal. These wines thus seem to consist predominantly of molecular contributions with most of the precipitable, large particles having been removed (say, above 500 nm). These two wines were judged to have superior relative taste and their manufacturers have obviously devoted considerable effort to preparing them. Although wine B, for example, produced about as much total light scattering as wines F and G, its DLS pattern is irregular and considerably steeper than the patterns of the other two. Its relative taste quality did turn out to be rather poor.

The DLS pattern of wine C was also quite noisy (large particulates present, though at substantially lower concentrations than A, B, D, and E), yet its overall pattern was depressed—even relative to F and G. It contains, therefore, smaller molecules than either F or G, probably smaller than needed to produce a good body. Had its manufacturer devoted more attention to the removal of the larger particulates, wine C could well have had a taste quality exceeding both F and G since these large particulate residues seem to correlate with poor quality.

The recorded DLS patterns could be used, therefore, as graphical representations of the associated wine's particulate properties. By recording several DLS patterns from each examined specimen, the patterns could be averaged and their overall fluctuations calculated. This latter calculation is a useful quantitative representation of the particulate fluctuations present. From a catalog of such curves and their fluctuations, the consumer could identify properties corresponding to his sensory preferences and thereby select wines without having to purchase and open them. In this way, his resulting choice would be rendered objective and not subject to the hyperbole of the manufacturers or professionals. The DLS patterns may also be quantified, for example by means of a polynomial decomposition of the type discussed in U.S. Pat. No. 3,928,140. The resultant coefficients, perhaps referenced to some standard values, could then be used by the consumer to compare his preferred values with those of the wine whose purchase he is considering.

While preferred embodiments of the invention have been disclosed and described, as previously noted, various other embodiments may be preferred by others skilled in this art. Accordingly, the scope of the invention is not limited to the preferred embodiment.

What is claimed:

1. A method for deriving a quantitative measure of a beverage that will correlate to the subjective sensory stimuli response of beverage consumers or producers comprising the steps of:
   (a) preparing an aliquot of the beverage sample;
   (b) illuminating the aliquot or a dilution thereof with a beam of monochromatic light;
   (c) detecting intensities of light scattered by the aliquot at a sufficient number of angles to obtain a characteristic scattering pattern arising from the particles present in the aliquot;
   (d) recording or storing said pattern;
   (e) quantitatively comparing said scattering pattern to a reference pattern or level;
   (f) using the quantitative difference of said light scattering pattern relative to the said reference light scattering pattern as a quantitative measure of said beverage.

2. A method as set forth in claim 1 in which the beverage is a wine.

3. A method as set forth in claim 1 in which the illuminating light is coherent.

4. A method as set forth in claim 1 in which the light scattering measurement is made in a single plane.

5. A method as set forth in claim 4 in which the illuminating light is polarized in a plane substantially orthogonal to the plane of the light scattering measurement.

6. A method as set forth in claim 1 in which the light scattering patterns are recorded or stored on a logarithmic scale.

7. A method for deriving a quantitative measure of a beverage that will correlate to the subjective sensory stimuli response of beverage consumers or producers comprising the steps of:
   (a) preparing an aliquot of the beverage sample;
   (b) illuminating the aliquot or a dilution thereof with a beam of monochromatic light;
   (c) detecting intensities of light scattered by the aliquot at a sufficient number of angles to obtain a characteristic scattering pattern arising from the particles present in the aliquot;
   (d) recording or storing a selected numerical representation of said pattern, said numbers being derived from said detected pattern;
   (e) quantitatively deriving the differences of these numbers each with respect to a corresponding number at the same detection angle earlier derived and stored from a reference pattern;
   (f) using said set of numerical differences as a quantitative representation of said beverage.

8. A method as set forth in claim 7 in which the beverage is a wine.

9. A method as set forth in claim 7 in which the illuminating light is coherent.

10. A method as set forth in claim 7 in which the light scattering measurement is made in a single plane.

11. A method as set forth in claim 9 in which the illumating light is polarized in a plane substantially orthogonal to the plane of the light scattering measurement.

12. A method as set forth in claim 7 in which the numerical representations of said pattern is recorded or stored on a logarithmic scale.

13. A method as set forth in claim 7 in which the numbers corresponding to the reference pattern are chosen to correspond to those obtained from very small particles.

14. A method for deriving a quantitative measure of a beverage that will correlate to the subjective sensory stimuli response of beverage consumers or producers comprising the steps of:
   (a) preparing an aliquot of the beverage sample;
   (b) illuminating the aliquot or a dilution thereof with a beam of monochromatic light;
   (c) successively detecting and storing the intensities of light scattered by the aliquot at a selected set of angles over a period of time wherein the intensity at each selected angle of said set of angles is measured several times;
   (d) calculating the average of the intensities so detected at each of the selected angles;
   (e) calculating the fluctuation of each detected value with respect to each calculated average value;
   (f) correlating said set of fluctuations to the subjective sensory stimuli response of said beverage consumers or producers;
   (g) characterizing said beverage by means of the numerical set of the calculated fluctuation values at each angle detected.

15. The method as set forth in claim 14 in which the beverage is a wine.

16. A method as set forth in claim 14 in which the illuminating light is coherent.

17. A method as set forth in claim 14 in which the light scattering measurement is made in a single plane.

18. A method as set forth in claim 17 in which the illuminating light is polarized in a plane substantially orthogonal to the plane of the light scattering measurement.

* * * * *